(12) United States Patent
Zanini

(10) Patent No.: US 6,361,510 B1
(45) Date of Patent: Mar. 26, 2002

(54) USE OF ULTRASOUNDS FOR THE TREATMENT OF DECOMPRESSION SICKNESS

(76) Inventor: Giovanni Zanini, Via Cadut Della Liberta, 17 Valmadrera, Valdmadrera Lecco (IT)

( * ) Notice: Subject to any disclaimer, the term of this patent is extended or adjusted under 35 U.S.C. 154(b) by 0 days.

(21) Appl. No.: 09/623,417

(22) PCT Filed: Jan. 3, 2000

(86) PCT No.: PCT/IB00/00001

§ 371 Date: Sep. 19, 2000

§ 102(e) Date: Sep. 19, 2000

(87) PCT Pub. No.: WO00/40300

PCT Pub. Date: Jul. 13, 2000

(30) Foreign Application Priority Data

Jan. 5, 1999 (IT) .......................................... MI99A0007

(51) Int. Cl.[7] ................................................. A61N 7/00
(52) U.S. Cl. .......................................................... 601/2
(58) Field of Search .................................. 600/437, 439, 600/459; 601/2

(56) References Cited

U.S. PATENT DOCUMENTS 3,499,437 A * 3/1970 Balamuth ...................... 601/2
3,920,011 A   11/1975 Losee
5,255,682 A * 10/1993 Pawluskiewicz et al. ... 600/459
5,895,356 A    4/1999 Andrus et al.

FOREIGN PATENT DOCUMENTS

EP        0 774 276 A    5/1997

* cited by examiner

Primary Examiner—Ruth S. Smith
(74) Attorney, Agent, or Firm—Nixon & Vanderhye

(57) ABSTRACT

Decompression sickness in human patients is treated by administering to the patient in the region affected by decompression sickness ultrasound energy having a frequency in the range of 1 to 15 MHz in an amount and time sufficient to alleviate the symptoms of decompression sickness.

4 Claims, No Drawings

USE OF ULTRASOUNDS FOR THE TREATMENT OF DECOMPRESSION SICKNESS

TECHNICAL FIELD

The present invention is concerned with the use of ultrasound for the treatment of decompression sickness. Another object of the present invention is an apparatus emitting ultrasounds able to be used for the above treatment.

BACKGROUND OF THE INVENTION

It is generally acknowledged that decompression sickness is caused by bubbles of inert gas in the blood and tissues due to a too rapid pressure reduction in the environment.

The presence of gaseous bubbles in the body can produce mechanical effects, such as distortion or pressure in the tissues, while the presence of bubbles inside the blood circulation can cause a reduction in the blood supply for the interested organs, until an infarct occurs.

Furthermore, the bubbles can produce biochemical effects such as activating coagulation, fibrinolysis or complement.

The variety and severity of symptoms depend upon bubble volume and location in the human body. Decompression sickness can be very mild in intensity and normally it is resolved without intervention. It is characterized by pain in the joints, muscles spindles, periosteum, and nerve sheaths with skin spots, lymphatic and symptoms as general malaise, anorexia and fatigue. Sometimes such symptoms precede a more serious sickness, which requires rapid and intensive treatment, characterized by problems in the central or peripheral nervous system and cardiorespiratory system which if not treated can provoke serious disability or even death.

Animal experiments and autopsies of divers and caisson workers by L. Hill et al (Caisson sickness and the physiology of work in compressed air. London, Arnold 1912) and others at the beginning of the century led to the conclusion that decompression sickness is caused by bubbles of inert gas in the blood and tissues.

Studies by Hills and Powell suggest that only 5 or 10 percent of the inert gas absorbed during normal diving can be released as bubbles after decompression. While this may seem a small fraction, it agrees with both in vitro and vivo observations that bubble formation is not widespread but is limited to discrete nucleation sites, whose number fluctuates with changing environmental and physiological conditions.

These phenomena are illustrated in observations of bubbles formed under the transparent shells of shrimps during an experiment performed by Daniels (Daniels S, Estaugh K C, Paton W D M, Smith E B, Micronuclei and bubbles formation: a quantitative study using the common shrimps, crangon cragnon. In Bachrach A J, Matzen M M: Underwaterphysiology VIII. Bethesda, Undersea Medical Society, 1984), who decompressed shrimp from sea level to altitude. Bubble formation rose with increasing altitude.

In addition Evans and Walder (Evans A, Walder D N. Significance of gas micronuclei in the etiology of decompression disease. Nature, 1969 222:251–252) found that bubble formation increased with exercise through a mechanism known as tribonucleation. Triconucleation (Hayward A T J. Tribonucleation of bubbles. Br. J. Appl. Phys. 18:641–664, 1967) causes bubble formation as a result of large negative pressures generated by viscous adhesion between surfaces separating in liquid. These negative pressures place the liquid in tension and may cause either spontaneous bubble formation or bubble formation from gas nuclei.

Bubbles created by tribonucleation can persist and act as gas nuclei for later bubble formation. The lifetime of such a nucleus is determined by the rate at which it dissolves. Mechanisms that stabilize a nucleus against surface tension can prolong its lifetime. Proposed stabilization mechanisms include gas in hydrophobic crevices and surface-active shells around bubbles. Such shells have been observed surrounding bubbles in seawater.

While it is unclear whether stabilization mechanisms play a role in decompression sickness, the evidence strongly suggests that the creation and destruction of gas nuclei are in dynamic equilibrium. Exercise shifts this equilibrium toward creation, more bubbles form and the risk of decompression sickness increases. The risk increases, on the other hand, if pressure treatment shifts the balance toward destruction.

The actual treatment for the decompression sickness is primarily compression chamber treatment.

A major determinant of a successful outcome is shortening the time from onset of symptoms to compression chamber treatment.

Many factors can extend this range of time such as a misevaluation of symptoms, the time for reaching the compression chamber and the quality of the medical care during transportation.

DISCLOSURE OF THE INVENTION

It was surprisingly found and it is an object of the present invention that the simple application of ultrasound destructs bubbles and then solves the above cited problems.

It is already known that echographic examination is one of the most popular imaging techniques due to its low price and overall it is safe to be used in pregnancy. Exposure to the ultrasound in fact has no collateral effects even if prolonged and the unique risk is a heat feeling produced by the lost energy during the passage in the body.

We have found that application of ultrasound at the frequency normally used for the echographic diagnosis (1–15 MHz) and at a mechanical index or power in a limit accepted by the FDA for diagnostic ultrasound equipment can destroy the gaseous bubbles.

The ultrasound, such as all the waves, has its own energy that can be released once in contact with the bubbles, destroying them. The oscillation produced by a resonance frequency can provide further destruction of the microbubbles, and substantially accelerates the destruction.

In conclusion the ultrasound can destroy the gaseous bubbles and regulating the level of the ultrasound energy and frequency can control such destruction.

Another object of the present invention is an apparatus having an ultrasound emission frequency comprised between 1 and 15 MHz and provided with a probe.

The transmission power and mechanical index of such apparatus is obviously in accordance with the pharmacopoeia requirements necessary for human and animal treatment.

The probe must have the characteristics of being able to be applied and transmit easily the ultrasound in the regions affected by the sickness.

Particularly preferred is the use of the above apparatus in diving centers. From a practical point of view, any diving center could have such portable apparatus, with energy able to destroy the gaseous bubbles and to control the automatic elimination of such bubbles from the body.

Any diver who complains of decompression sickness symptoms could be exposed to ultrasound, on the target organs for an interval/s of sufficient duration to allow disappearance or reduction of the symptoms or enough while seeking other treatment to reach the compression chamber.

Obviously, the use of the apparatus can be followed by anyone, independently from his/her medical knowledge.

For instance, a diver complaining joint pain could be exposed to an ultrasound beam directed on the painful joints until the disappearance of the pain.

Considering the physiopathology of decompression sickness the ultrasound treatment can solve the minor symptoms without further intervention. For the more serious they could assist the usual interventions of first aid, such as fluid, oxygen and corticosteroid administration during the victim's transportation to the compression chamber, decreasing the symptoms and probably improving the prognosis.

In fact, in the first case tissue supersaturation should be at a lower level with respect to those present in subjects with more serious symptoms, then the prolonged insonation should be enough to preclude any problem until reaching an equilibrium between the inert gas concentration in the tissues, the blood and the environment.

In the more serious cases, where presumably supersaturation in the tissues is at a higher level, the use of the ultrasound destroys the bubbles at organ level thereby decreasing the symptoms, but it can not prevent reconstruction. Then a dynamic process is created to improve the subject's prognosis in order to reach the compression chamber in better condition.

The efficacy of the present invention is shown in the following example performed analogously to what was previously cited.

EXAMPLE 10 living shrimps are placed in a compression chamber where a 40% pressure reduction with respect to the atmosphere is done in 5 minutes. The formation of gaseous bubbles under their shells is visible which, after sonication with a suitable apparatus, disappear.

What is claimed is:

1. A method of treating decompression sickness in a human patient comprising administering to said patient in the region affected by decompression sickness ultrasound energy having a frequency in the range of 1 to 15 MHz in an amount sufficient to alleviate the symptoms of decompression sickness.

2. The method of claim 1 wherein ultrasound energy is applied to the patient's affected joints.

3. A method of dissipating microbubbles of gas in the blood or tissues of a human patient suffering from decompression sickness, said method comprising administering to the patient in a region affected by decompression sickness ultrasound energy having a frequency in the range of 1 to 15 MHz to dissipate the microbubbles of gas and alleviate the patient's symptoms.

4. The method of claim 3 wherein ultrasound energy is applied to the patient's affected joints.

* * * * *